(12) United States Patent
Ku et al.

(10) Patent No.: US 6,822,101 B2
(45) Date of Patent: Nov. 23, 2004

(54) PROCESS FOR PREPARING AMINE-SUBSTITUTED BENZOFURANS

(75) Inventors: Yi-Yin Ku, Buffalo Grove, IL (US); Yu-Ming Pu, Gurnee, IL (US); Marlon D. Cowart, Round Lake Beach, IL (US); Timothy A. Grieme, Chicago, IL (US); Ashok K. Gupta, Gurnee, IL (US); Daniel J. Plata, Wadsworth, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/654,897

(22) Filed: Sep. 5, 2003

(65) Prior Publication Data

US 2004/0133007 A1 Jul. 8, 2004

Related U.S. Application Data

(60) Provisional application No. 60/411,210, filed on Sep. 16, 2002.

(51) Int. Cl.$^7$ ............................................. C07D 407/06
(52) U.S. Cl. ....................................... 548/525; 546/196
(58) Field of Search ........................... 546/196; 548/525

(56) References Cited

U.S. PATENT DOCUMENTS

2002/0183309 A1   12/2002   Bennani et al. ........ 514/217.03

FOREIGN PATENT DOCUMENTS

| EP | 0 567 967 | 4/1993 |
| EP | 0 721 947 | 7/1996 |
| WO | 02/74758 | 9/2002 |
| WO | 03/059342 | 7/2003 |

OTHER PUBLICATIONS

Kelly, "Laterally substituted phenyl benzoates incorporating a trans–1,4–disubstituted cyclohexane ring," Helvetica Chimica Acta 72(3):594–607 (1989).

Black et al., "2,3–Diarylcyclopentenones as orally active, highly selective cyclooxgenase–2 inhibitors," J. Med. Chem. 42:1274–1281 (1999).

Carroll et al., "Synthesis, nicotinic acetylcholine receptor binding, and antinociceptive properties of 2–exo–3–(2'–substituted 5'–pyridinyl)–7–azabicyclo[2.2.1] heptanes. Epibatidine analogues," J. Med. Chem. 44:2229–2237 (2001).

Gronowitz et al., "On the synthesis of various thienyl–and selenienylpyrimidines," Chem. Scr. 26(2):305–309 (1986).

Letsinger et al., "Organoboron compounds. IX. 8–quinolineboronic acid, its preparation and influence on reactions of chlorohydrins," J. Amer. Chem. Soc. 81(2):498–501 (1959).

O'Neill et al., "Total synthesis of (±)–cytisine," Organic Letters 2(26):4201–4204 (2000).

Sindkhedkar et al., "Aromatic interactions in the synthesis and conformation of two collapsible tetracationic cyclophanes," Tetrahedron 57:2991–2996 (2001).

Takagi et al., "Iridium–catalyzed C–H coupling reaction of heteroaromatic compounds with bis(pinacolato)diboron: regioselective synthesis of heteroarylboronates," Tetrahedron Letters 43:5649–5651 (2002).

Umemoto et al., "Molecular paneling by coordination: an $M_{15}L_6$ hexahedral molecular capsule having clefts for reversible guest inclusion," Angew. Chem. Int. Ed. 40(14):2620–2600 (2001).

Primary Examiner—Patricia L. Morris
(74) Attorney, Agent, or Firm—Portia Chen

(57) ABSTRACT

The present invention relates to processes for preparing amine substituted benzofurans, and more particularly 4-(2-{2-[(2R)-2-methyl-1-pyrrolidinyl]ethyl}-1-benzofuran-5-yl)benzonitrile, and salts thereof. Compounds prepared by the processes of the invention have demonstrated activity as histamine-3 receptor ligands.

5 Claims, No Drawings

US 6,822,101 B2

PROCESS FOR PREPARING AMINE-SUBSTITUTED BENZOFURANS

This application claim the benefit of provisional application No. 60/411,210, filed 16 Sep. 2002.

BACKGROUND OF THE INVENTION

1. Field of the Invention

The present invention relates to processes for preparing amine-substituted benzofuran compounds, and more particularly, 4-(2-{2-[(2R)-2-methyl-1-pyrrolidinyl]ethyl}-1-benzofuran-5-yl)benzonitrile and salts thereof, as well as intermediates in such processes. The compounds have demonstrated activity as histamine-3 receptor ligands.

2. Description of Related Technology

Benzofuran derivatives, particularly amine-substituted benzofuran derivatives such as 2-(2-aminoethyl)-substituted benzofuran compounds, have demonstrated activity as histamine-3 ($H_3$) receptor ligands. Histamine-3 receptor ligands provide useful compounds for pharmaceutical products. For example, $H_3$ receptor ligands can be used for treatment of disorders related to cardiovascular processes, memory processes, such as Alzheimer's disease and attention-deficit hyperactivity disorder, neurological processes, cancer, sleep processes, and weight regulation, among other conditions. One particular compound, having the structure

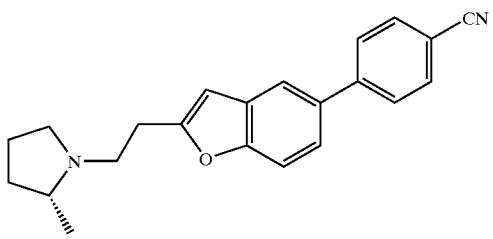

and the IUPAC name 4-(2-{2-[(2R)-2-methyl-1-pyrrolidinyl]ethyl}-1-benzofuran-5-yl)benzonitrile demonstrates promising activity for use as a pharmaceutically active $H_3$-receptor ligand. The compound has demonstrated promising activity for enhancing learning and cognition. The compound, related derivatives thereof, and processes for preparing the compound and derivatives are described in commonly-owned copending U.S. patent applications Ser. No. 09/810,648, filed Mar. 16, 2001; Ser. No. 10/044,495, filed Jan. 11, 2002; and Ser. No.10/081,207, filed Feb. 22, 2002.

Previous processes for preparing 2-(2-aminoethyl)-substituted benzofuran compounds generally involve halogenation of a starting phenol by treatment with sodium iodide and sodium hypochlorite, preferably in the presence of a base. The resulting iodinated phenol is subsequently converted into a functionalized benzofuran and the desired amine is appended. Many steps of the previous processes required chromatographic isolation and purification of intermediate compounds to provide a material possessing suitable qualities of purity and economy for the preparation of a pharmaceutical compound. Although such processes provide beneficial methods for preparing amine-substituted benzofuran compounds, and particularly, 4-(2-{2-[(2R)-2-methyl-1-pyrrolidinyl]ethyl}-1-benzofuran-5-yl)benzonit it would be beneficial to provide processes for preparing such compounds while reducing or eliminating isolation and purification steps and/or increasing reaction product yield. Such processes would provide for efficient, beneficial preparation of high-grade pharmaceutical compounds.

Accordingly, there remains a need to provide improved processes for making amine-substituted benzofurans. It would be beneficial to provide a process for preparing 4-(2-{2-[(2R)-2-methyl-1-pyrrolidinyl]ethyl}-1-benzofuran-5-yl) in particular, and salts thereof.

SUMMARY OF THE INVENTION

In one embodiment, the invention relates to a process for preparing compounds of the formula (I)

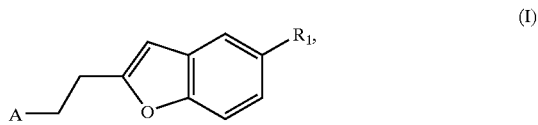

or a salt thereof, wherein

A is heterocycle selected from pyrrolidinyl or piperidinyl, wherein the heterocycle is substituted with 0,1, 2, 3, or 4 substituents selected from the group consisting of alkyl and fluoroalkyl; and $R_1$ is 4-cyanophenyl, aryl, or heteroaryl, wherein the phenyl of 4-cyanophenyl, aryl, or heteroaryl is substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl.

The process comprises treating a compound of formula (II)

wherein $R_A$ is selected from the group consisting of bromo, chloro, 4-cyanophenyl, aryl, and heteroaryl, and the phenyl portion of the 4-cyanophenyl, the aryl, and the heteroaryl can be substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl, with a halogenating reagent selected from halogenating agents of the formula

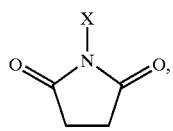

wherein X is bromo or iodo, N-iodoacetamide, N-bromoacetamide, N-iodophthalimide, N-bromophthalimide, iodine, bromine, ICl, IBr, BrCl, or an alkaline iodide or bromide with an oxidant, such as NaI and hydrogen peroxide, to provide a compound of formula (III)

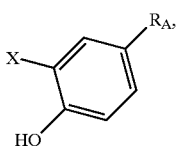

(III)

wherein $R_A$ and X are as previously defined.

Compounds of formula (III) are treated with 3-butyn-1-ol to provide a compound of formula (IV)

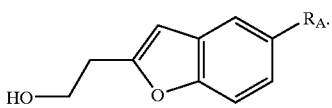

(IV)

Compounds of formula (IV) are treated with a sulfonating reagent to provide a compound of formula (V)

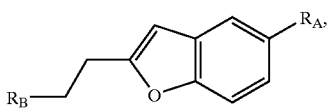

(V)

wherein $R_B$ represents a toluenesulfonate, methanesulfonate, or trifluoromethanesulfonate group. In addition, compounds of formula (III) are treated with a toluenesulfonyl butanol to provide (V), wherein $R_B$ represents a toluenesulfonate group, directly.

Compounds of formula (V) are treated with an amine reagent, preferably selected from the group consisting of pyrrolidine and piperidine, wherein the pyrrolidine or piperidine is substituted with 0, 1, 2, 3, or 4 substituents selected from the group consisting of alkyl and fluoroalkyl to provide compounds of formula (VI),

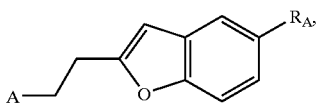

(VI)

wherein $R_A$ is bromo, chloro, 4-cyanophenyl, aryl, or heteroaryl. The phenyl moiety of 4-cyanophenyl and aryl and the heteroaryl can be substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl. Wherein $R_A$ in a compound of formula (VI) is 4-cyanophenyl, aryl, or heteroaryl, the reaction provides compounds within the scope of formula (I).

Compounds of formula (III), (IV), (V), or (VI) wherein $R_A$ is bromo or chloro, can be treated with a boronic acid reagent of formula (VIII)

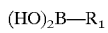

(VIII)

or a boronate ester compound of the formula (VIII-a)

(VIII-a), wherein $R_1$ is 4-cyanophenyl, aryl, or heteroaryl, wherein the phenyl of 4-cyanophenyl, the aryl, and the heteroaryl are substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl; and $R_e$ and $R_f$ are each independently alkyl or $R_e$ and $R_f$ are taken together to form a ring, wherein the ring is substituted with 0, 1, 2, 3, or 4 substituents selected from the group consisting of alkyl or aryl, which can be substituted as previously described for compounds of formula (I), to provide the corresponding product wherein $R_A$ is replaced by a substituent represented by $R_1$. Wherein $R_A$ in a compound of formula (VI) is bromo or chloro, the reaction provides compounds within the scope of formula (I).

In another embodiment, the invention relates to a process for preparing compounds of formula (I), as defined above, comprising at least the step of treating a compound of the formula:

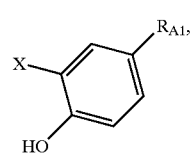

(III-a)

wherein $R_{A1}$ is selected from the group consisting of bromo, chloro, 4-cyanophenyl, aryl, and heteroaryl, and the phenyl portion of the 4-cyanophenyl, the aryl, and the heteroaryl can be substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl, and X is bromo or iodo, with a compound of formula (VII)

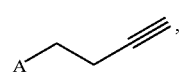

(VII)

wherein A is a heterocyclic group selected from the group consisting of pyrrolidinyl and piperidinyl, and the heterocyclic group can be substituted with 0, 1, 2, 3, or 4 substituents selected from the group consisting of alkyl and fluoroalkyl, to provide a compound of formula (VI-a)

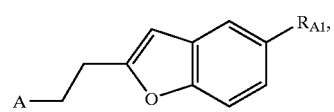

(VI-a)

wherein A and $R_{A1}$ are as defined for compounds of formula (VII) and (III-a), respectively. Typically, the reaction is carried out using a palladium catalyst, metal halide, and base, wherein the palladium catalyst can be a palladium(0) or a palladium(II) catalyst, for example, tetrakis(triphenylphosphine)palladium, tris(dibenzylideneacetate) dipalladium, $PdCl_2(Ph_3P)_2$, and the like.

Compounds of formula (VI-a), wherein $R_{A1}$ is bromo or chloro, can be treated with a compound of formula (VIII)

(VIII), or a compound of formula (VIII-a)

(VIII-a), wherein $R_1$, $R_e$ and $R_f$ are as previously described, to provide compounds of formula (I). Particularly, it is preferred that $R_1$ is 4-cyanophenyl. Compounds of formula (VI-a), wherein $R_{A1}$ is 4-cyanophenyl, aryl, or heteroaryl, are within the scope of compounds of formula (I), as previously described.

In yet another aspect, the invention relates to a process for preparing a compound useful in the preparation of 2-(2-aminoethyl)-substituted benzofuran compounds demonstrating activity as $H_3$-receptor ligands. The process comprises the step of treating a compound of formula (II)

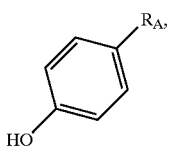

(II)

wherein $R_A$ is selected from the group consisting of bromo, chloro, 4-cyanophenyl, aryl, and heteroaryl, as previously defined, with a halogenating reagent of the formula:

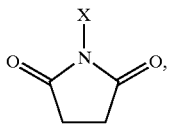

wherein X is bromo or iodo, to provide a compound of formula (III)

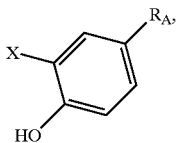

(III)

wherein $R_A$ is as described for compounds of formula (II). The reaction is particularly useful in preparing a compound of formula (III) wherein X is iodo or bromo and $R_A$ is 4-cyanophenyl, which can be used in preparing 2-(2-aminoethyl)-substituted benzofuran compounds, particularly 4-(2-{2-[(2R)-2-methyl-1-pyrrolidinyl]ethyl}-1-benzofuran-5-yl)benzonitrile.

The processes, and compounds prepared by the processes, including intermediate compounds, are further described herein.

DETAILED DESCRIPTION OF THE PRESENT INVENTION

A number of terms are used herein to designate particular elements of the present invention. When so used, the following meanings are intended.

The term "fluoroalkyl" as used herein, means at least one fluorine atom is attached to the parent molecular moiety through an alkyl group, as defined herein. Representative examples of fluoroalkyl include, but are not limited to, fluoromethyl, 2-fluoroethyl, trifluoromethyl, 2,2,2-trifluoroethyl, and pentafluoroethyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkyl," as used herein, refers to a straight or branched chain hydrocarbon containing from 1 to 10 carbon atoms, and preferably 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylthio," as used herein, refers to an alkyl group, as defined herein, appended to the parent molecular moiety through a sulfur atom, as defined herein. Representative examples of alkylthio include, but are not limited to, methylsulfanyl, ethylsulfanyl, tert-butylsulfanyl and hexylsulfanyl.

The term "alkylthioalkyl," as used herein, refers to an alkylthio group, as defined herein, appended to the parent molecular moiety through an alkyl group. The alkylthio group typically is appended to the alkyl group via a sulfur atom. Representative examples of alkylthio include, but are not limited to, methylsulfanylmethyl, ethylsulfanylmethyl, tert-butylsulfanylmethyl and hexylsulfanylmethyl.

The term "aryl," as used herein, refers to a phenyl ring substituted with 0, 1, 2, 3, or 4 substituents independently selected from alkoxy, alkoxyalkyl, alkyl, alkylcarbonyl, alkylthio, alkylthioalkyl, cyano, haloalkoxy, and haloalkyl. Examples of aryl include, but are not limited to, 4-cyanophenyl, 4-chlorophenyl, 4-methylphenyl, 4-phenylethanone, 4-trifluoromethylphenyl, 4-trifluormethoxyphenyl, and the like.

The term "cyano," as used herein, refers to a —CN group.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, fluoromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from N, O, or S. The five-membered rings can have two double bonds or are a tautomer of a 5-membered ring having two double bonds. The six-membered rings have three double bonds or are a tautomer of a 6-membered ring having three double bonds. The term "heteroaryl" also includes bicyclic systems wherein the aromatic five- or six-membered ring is fused to a phenyl group. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, quinolyl, tetrazolyl, thiadiazolyl, thiazolyl, thienyl, triazolyl, and triazinyl. The heteroaryl groups of the present invention are substituted with 0, 1, 2, 3, or 4 substituents independently selected from alkoxy, alkoxyalkyl, alkyl, alkylthio, alkylthioalkyl, cyano, haloalkoxy, and haloalkyl.

The term "heterocycle" or "heterocyclic group", as used herein, refers to a saturated five- or six-membered ring containing a nitrogen atom. The heterocycle can be substituted with 0, 1, 2, 3, or 4 substituents selected from alkyl and fluoroalkyl. Representative examples of heterocycle include, but are not limited to, 2-methylpyrrolidinyl, 2-fluoromethylpyrrolidinyl, pyrrolidinyl, and piperidinyl.

The term "hydroxy", as used herein, refers to an —OH group.

The invention provides processes for preparing amine-substituted benzofuran derivatives and, more particularly, 2-(2-aminoethyl)-substituted benzofuran compounds. The compounds prepared by the processes of the invention can have the formula (I),

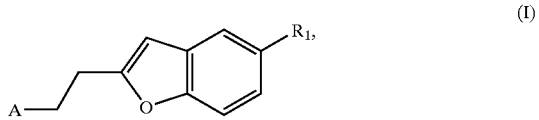

wherein A is a heterocycle selected from pyrrolidinyl or piperidinyl, wherein the heterocyclic group is substituted with 0, 1, 2, 3, or 4 substituents selected from the group consisting of alkyl and fluoroalkyl; and $R_1$ is 4-cyanophenyl, aryl, or heteroaryl, wherein the phenyl of 4-cyanophenyl and aryl, or the heteroaryl, is substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl. Such compounds have demonstrated activity as $H_3$-receptor ligands.

The heterocyclic group for A is a saturated nitrogen ring, and preferably contains five or six members, including the nitrogen atom. Examples of rings represented by the group A in a compound of formula (I) include, but are not limited to, pyrrolidinyl and piperidinyl. The heterocyclic group, particularly the pyrrolidinyl group, also can be substituted with substituents on the ring, for example, alkyl, fluoroalkyl, and the like. Examples of substituted heterocyclic groups are 2-methylpyrrolidinyl, including (2R)-2-methylpyrrolidine and (2S)-2-methylpyrrolidine, 2-ethylpyrrolidinyl, and the like. The preferred heterocyclic group for A in a compound of formula (I) is (2R)-2-methylpyrrolidine.

The heteroaryl group in compounds of formula (I), as represented by $R_1$, represents an aromatic five- or six-membered ring wherein 1, 2, 3, or 4 heteroatoms are independently selected from N, O, or S. Typically, the five-membered rings have two double bonds or are tautomers of five-membered rings with two double bounds. Typically, the six-membered rings have three double bonds or are tautomers of six-membered rings having three double bonds. The invention also contemplates heteroaryl groups wherein the aromatic five- or six-membered ring is fused to a phenyl group. Examples of heteroaryl groups suitable for compounds of formula (I) include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, quinolyl, tetrazolyl, thiadiazolyl, thiazolyl, thienyl, triazolyl, triazinyl, and the like. The preferred heteroaryl groups are pyrimidinyl, pyrazinyl, and pyrazolyl.

The heteroaryl groups of the present invention can be substituted with 0,1, 2, 3, or 4 substituents independently selected from alkoxy, alkoxyalkyl, alkyl, alkylthio, aikylthioalkyl, cyano, haloalkoxy, halogen, and haloalkyl.

The aryl group in compounds of formula (I), as represented by $R_1$, can include, but are not limited phenyl groups substituted with 0, 1, 2, 3, or 4 substituents selected from the group consisting of alkoxy, alkoxyalkyl, alkyl, alkylcarbonyl, alkylthio, alkylthioalkyl, cyano, haloalkoxy, halogen, and haloalkyl. Examples of aryl include, but are not limited to, 4-cyanophenyl, 4-chlorophenyl, 4-methylphenyl, 4-phenylethanone, 4-trifluoromethylphenyl, 4-trifluormethoxyphenyl, and the like.

The compounds are described, inter alia, in commonly-owned copending U.S. patent applications Ser. No. 09/810,648, filed Mar. 16, 2001; Ser. No. 10/044,495, filed Jan. 11, 2002; and Ser. No. 10/081,207, filed Feb. 22, 2002, each of which is incorporated by reference herein. The processes of the invention particularly are useful for preparing 4-(2-{2-[(2R)-2-methyl-1-pyrrolidinyl]ethyl}-1-benzofuran-5-yl) benzonitrile having the structure

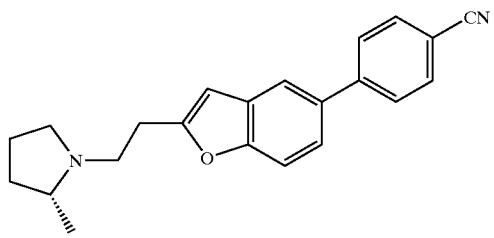

and salts thereof including, but not limited to, tartrate salts, for example (L)-tartrate.

Examples of processes of the invention are described herein in the following Schemes 1–7. The Schemes are intended to illustrate a process of the invention and are not meant to limit the scope of the invention in any way. Isomeric forms of compounds described in the Schemes also are contemplated and considered within the scope of the invention.

Abbreviations used in the descriptions of the Schemes and the Examples that follow are: DMSO for dimethylsulfoxide; EtOH for ethanol; IPAC for isopropyl acetate; HPLC for high pressure liquid chromatography; Ph for phenyl; and TsO for toluenesulfonate.

Scheme 1

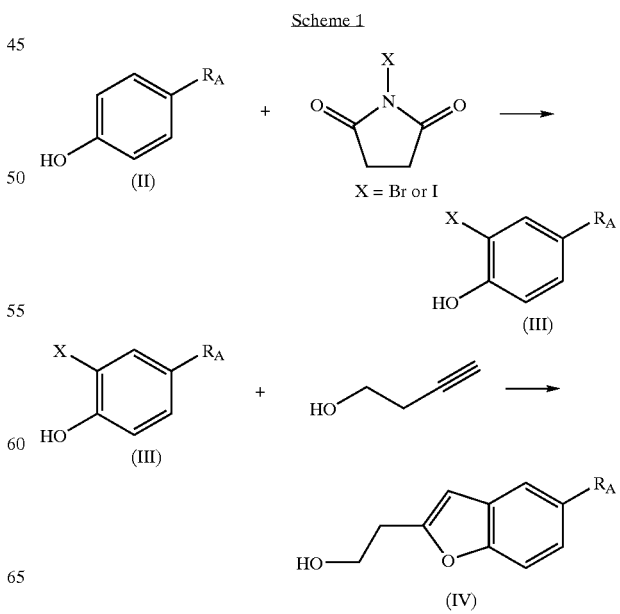

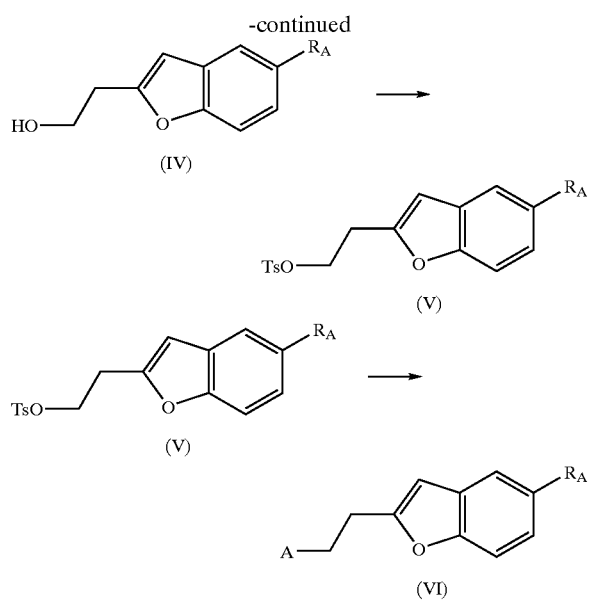

As shown in Scheme 1, compounds of formula (II) can be treated with a halogenating reagent to provide a compound of formula (III). Compounds of formula (II) are those wherein $R_A$ represents bromo, 4-cyanophenyl, aryl, or heteroaryl, wherein the phenyl portion of 4-cyanophenyl, the aryl, or the heteroaryl group can be substituted with various substituents. Examples of suitable substituents can include, for example, alkoxy, alkoxyalkyl, alkyl, alkylthio, alkylthioalkyl, cyano, haloalkoxy, halogen, and haloalkyl.

Typically, the compound of formula (II) is purchased commercially or prepared from commercially available 4-bromophenol. For example, 4-bromophenol can be treated with heteroarylboronic acids or heteroaryl boronate esters and a palladium complex and a phosphine in the presence of a base to provide suitable starting materials for the process, wherein $R_A$ is 4-cyanophenyl or heteroaryl. Examples of palladium complexes suitable for preparing a compound of formula (II) include, but are not limited to, tetrakis (triphenylphosphine)palladium(0) and palladium acetate. The phosphine can include, but is not limited to, 2-(dicyclohexylphosphino)biphenyl and 2-(dicyclohexylphosphino)biphenyl. Preferably, the reaction is carried out in the presence of a base for example, sodium carbonate or potassium phosphate, at above room temperature. Examples of more specific conditions for accomplishing the reaction include treating the 4-bromophenol with a heteroarylboronic acid, tetrakis(triphenylphosphine) palladium(0) and 2-(dicyclohexylphosphino)biphenyl in a solvent mixture of water and 1,2-dimethoxyethane, isopropyl alcohol, or toluene, at about 40° C. to about 100° C. The reaction typically is accomplished in about 1 to about 36 hours. Examples of commercially available heteroarylboronic acids are 4-cyanophenyl boronic acid, pyridine-3-boronic acid, and the like.

Compounds of formula (II), wherein $R_A$ represents bromo, chloro, 4-cyanophenyl, or heteroaryl, as described above, can be treated with a halogenating reagent selected from N-iodosuccinimide or N-bromosuccinimide and an acid as shown in Scheme 1. Alternative halogenating agents include, but are not limited to, N-iodoacetamide, N-bromoacetamide, N-iodophthalimide, N-bromopthalimide, iodine, bromine, ICl, IBr, BrCl, an alkaline iodide or bromide with an oxidant such as with NaI and hydrogen peroxide. The amount of halogenating reagent suitable for the reaction can include from about 1 to about 3 molar equivalents relative to the amount of compound having the formula (II). A preferred amount of halogenating reagent is from about 0.90 to about 1 molar equivalent of the succinimide. Preferably, about 1 mole of halogenating reagent is used for each mole of the compound of formula (II). Preferably, the reaction is accomplished in an organic solvent or in a weak acid in the presence of a catalytic amount of strong acid. A specific example of a suitable solvent is acetonitrile. A weak acid suitable for the reaction is acetic acid in the presence of a strong acid, for example, sulfuric acid, trifluoroacetic acid, and trifluoromethanesulfonic acid. Particularly, N-iodosuccinimide is reacted with the compound of formula (II) in acetic acid in the presence of a stronger acid, such as sulfuric acid, while maintaining the reaction at or below room temperature, for example at or less than 27° C. A preferred amount of concentrated sulfuric acid is from about 0.025 to about 0.075 molar equivalents, relative to the starting material of formula (II). The preferred amount of sulfuric acid is about 0.05 equivalents.

Compounds of formula (III), wherein X is bromo or iodo and $R_A$ is as defined above, for example of formula (II), can be treated with an alkynol or a toluenesulfonyl alkynol, to provide benzofuran derivatives of formulae (IV) or (V), respectively. The coupling reaction is accomplished using a palladium source, a phosphine ligand for the palladium, and a metal halide in the presence of a base. The preferred alkynol is 3-butyn-1-ol, but compounds that provide alcohols equivalent to the 3-butyn-1-ol also can be used, for example alkynes that include protected forms of 3-butyn-1-ol, $R_pOCH_2CH_2C\equiv CH$, where the $R_p$ is a protecting group. Typical protecting groups are described for instance in Green and Wuts, "Protecting Groups in Organic Synthesis", 3rd edition, published by John Wiley and Sons, New York (1999), and which may be appended onto the 3-butyn-1-ol, and subsequently removed by the methods therein. In this case, removal of the protecting group $R_p$ in the product will generate compounds of structure (IV). Examples of specific protecting groups represented by $R_p$ include, but are not limited to, triethylsilyl, acetyl, benzoyl, and tetrahydropyran-2-yl. Typically, from about 1 to about 2 equivalents of the alkynol are used relative to one mole of the compound of formula (II). Examples of suitable palladium sources include, but are not limited to, palladium(II) acetate, tetrakis(triphenylphosphine)palladium, and tris (dibenzylideneacetate)dipalladium. The preferred palladium catalyst is palladium (II) acetate.

A phosphine suitable for the reaction can be triphenylphosphine. Other examples of phosphines suitable for the reaction can include, triphenylphosphine, bis (diphenylphosphine)methane, bis(diphenylphosphine) ethane, tri(o-tolyl)phosphine, and the like. The ratio of palladium catalyst to phosphine generally ranges from about 1:1 to about 1:8 relative to the palladium source. Preferably, about two molar equivalents of phosphine are used for one mole of the palladium source.

A useful metal halide is copper(I) iodide. Alternative and additional halides can include, but are not limited to, copper (I) bromide. Typically, the amount of metal halide used ranges from about 1:1 to about 1:2 relative to the phosphine. The reaction preferably is carried out in the presence of a base. Suitable bases include, but are not limited to, diisopropylamine, diethylamine, dipropylamine, triethylamine, isopropylethylamine, pyrrolidine, or piperidine, in a solvent including, but not limited to, isopropyl acetate to provide compounds of formula (IV).

Although the compound of formula (IV) can be isolated and separated by column chromatography, it is not necessary to isolate or purify the product to provide a useful starting material for the hydroxy protection step of preparing a compound of formula (V), which follows.

Compounds of formula (IV) can be treated with a sulfonating reagent in basic conditions to provide compounds of formula (V). Preferably, the sulfonating reagent provides a toluenesulfonyl group to activate the hydroxy group of a compound of formula (IV) as shown in Scheme 1. Examples of suitable sulfonating reagents can include, but are not limited to, para-toluensulfonic chloride and para-toluenesulfonic anhydride. Alternative sulfonating agents also can provide similarly reactive and useful products related to compounds of formula (V) when reacted with compounds of formula (IV). Such sulfonating agents can include, but are not limited to, methane sulfonic anhydride, methane sulfonyl chloride, and triflic anhydride, wherein the toluenesulfonyl moiety of a compound of formula (V) is replaced with a methansulfonyl or trifluoromethanesulfonyl group. Basic conditions to accomplish the reaction include, for example, treating the compound of formula (IV) with N,N-dimethylaminopyridine and a base. Suitable bases for the reaction can include, for example, triethylamine, pyridine, and the like. The preferred base is triethylamine. Suitable solvents for the reaction typically are aprotic solvents, for example acetonitrile, tetrahydrofuran, dichloromethane, and the like. Typically, the sulfonating reagent is reacted with the compound of formula (IV) in a range of from about 1:1 to about 1:5 molar equivalents, relative to the compound of formula (IV). Preferably, about 3 molar equivalents of sulfonating reagent are used for each mole of the compound of formula (IV). The reaction can be carried out in at least room temperature. Typically, the reaction will be accomplished in from about 1 to 2 hours. The product of formula (V) can be, but need not be, isolated and purified according to conventional methods for use in reaction attaching the amine.

Compounds of formula (V) can be reacted with an amine reagent to provide compounds of formula (VI). The preferred reagent is a cyclic amine reagent, for example pyrrolidine or piperidine. The reaction can be accomplished in a solvent, for example, acetonitrile, ethanol, methanol, isopropyl alcohol or a mixture thereof. The pyrrolidine or piperidine reagent can include 0, 1, 2, 3, or 4 substituents selected from the group consisting of alkyl and fluoroalkyl. Suitable amine reagents can be provided as the amine compound, for example, 2-methylpyrrolidine, or as a salt of the amine compound, such as 2-methylpyrrolidine tartrate. Examples of suitable amine reagents include, but are not limited to, 2-methylpyrrolidine, 2-ethylpyrrolidine, 2-fluoromethylpyrrolidine, and the salts thereof. Examples of suitable salts of the amine reagent include, but are not limited to, tartrate, lactate, chloride, and succinate salts. The reaction typically is accomplished in the presence of a weak base, for example, potassium carbonate, and the like. The preferred amine reagent for the reaction is pyrrolidine, including the (2R)-2-methylpyrrolidine enantiomer and the (2S)-2-methylpyrrolidine enantiomer. The more preferred enantiomer is (2R)-2-methylpyrrolidine.

In addition, the invention provides processes for preparing amine-substituted benzofuran compounds as shown below in Scheme 2.

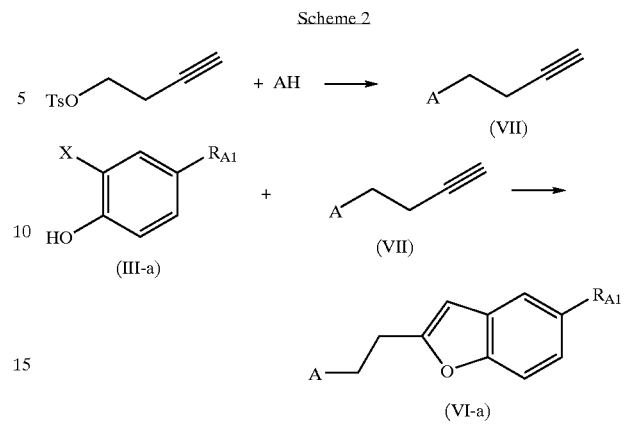

Scheme 2

As shown in Scheme 2, 3-butynyl4-methylbenzenesulfonate is reacted with an amine reagent of formula AH, wherein A represents a heterocyclic group selected from pyrrolidinyl or piperidinyl. The pyrrolidinyl group or the piperidinyl group can be substituted as previously described for the compound of formula (I).

Typically, the 3-butynyl-4-methylbenzenesulfonate, or 3-butynyl-4-toluenesulfonate, is prepared by treating 3-butyn-1-ol with a sulfonating reagent including, but not limited to, para-toluensulfonic chloride or para-toluenesulfonic anhydride, and a base. Examples of bases for the reaction can include, but not is limited to, triethylamine, as previously described. Suitable solvents for the reaction can include, but is not limited to, acetonitrile, tetrahydrofuran, or mixtures thereof. The conditions for the reaction are similar to those previously described for the protection of the compound of formula (IV) in Scheme 1, from which a compound of formula (V) is obtained.

3-Butynyl-4-methylbenzenesulfonate can be treated with the amine reagent in an aprotic solvent, preferably in the presence of base, to provide compounds of formula (VII). The reaction conditions are similar to those described for providing compounds of formula (VI) in Scheme 1. Particularly, the preferred base is potassium carbonate. The preferred solvent for the reaction includes, but is not limited to, acetonitrile, ethanol, methanol, isopropyl alcohol or a mixture thereof. Typically, the reaction is carried out at above room temperature, for example in a temperature of from about 80° C. to about 100° C. The preferred temperature for the reaction is about 85° C. The amine reagents also are similar to those previously described for coupling the amine group to compounds of formula (V) in Scheme 1. The preferred amine reagent is 2-methylpyrrolidine and, more particularly, the 2-methylpyrrolidine tartrate salt.

Compounds of formula (VII) can be treated with compounds of formula (III-a), wherein $R_{A1}$ is bromo or 4-cyanophenyl and the phenyl of 4-cyanophenyl is substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl, to provide compounds of formula (VI-a), wherein $R_{A1}$ is as defined for compounds of formula (III-a). The reaction is accomplished in a manner similar to the conditions described for the preparation of a compound of formula (IV) as previously described. The reaction is accomplished in the presence of a palladium catalyst, preferably a Pd(0) or Pd(II) catalyst in combination with a phosphine ligand for the palladium. Typically the reaction is carried out using a metal halide and a base. Examples of palladium catalysts can include, for example, Pd(Ph₃P)₄, Pd(dba), Pd₂(dba)₃, Pd(Pcy₃)₂, Pd(dppe), Pd(dppf), PdCl₂(Ph₃P)₂, PdCl₂(dppf)₂, PdCl₂(dppe)₂, and PdCl₂(CH₃CN)₂. As used herein, the preceding designations are intended to refer to the following: Pd(Ph₃P)₄ for tetrakis(triphenylphosphine)palladium, Pd(dba) for (dibenzylideneacetate)palladium, Pd₂(dba)₃ for tris(dibenzylideneacetate)d ipalladium, Pd(Pcy₃)₂ for bis(tricyclohexylphosphine)palladium, Pd(dppe) for (2-(diphenylphosphino)ethyl)palladium, Pd(dppf) for (1,1'-bis(diphenylphosphino)ferrocene)palladium, PdCl₂(Ph₃P)₂ for bis(triphenylphosphine)dichloropalladium, PdCl₂(dppf)₂ for bis(1,1'-bis(diphenylphosphino)ferrocene)palladium, PdCl₂(dppe)₂ for bis(2-(diphenylphosphino)ethyl) dichloropalladium, and PdCl₂(CH₃CN)₂ for dichlorobis(acetonitrile)palladium. More specifically, preferred palladium sources include, but are not limited to, tetrakis(triphenylphosphine)palladium, tris(dibenzylideneacetate) dipalladium, and PdCl₂(Ph₃P)₂. Preferably, the palladium catalyst is PdCl₂(Ph₃P)₂.

Suitable phosphine ligands that can be coordinated with the palladium catalyst are, for example, triphenylphosphine, bis(diphenylphosphine)methane, bis(diphenylphosphine) ethane, tri(o-tolyl)phosphine, and the like. The reaction may, but need not, include the use of a phosphine ligand, depending on the palladium catalyst used. Typically, palladium catalysts already coordinated with a phosphine ligand are not used in combination with additional phosphine ligands.

Although copper(I) chloride and copper(I) bromide may be suitable, the preferred metal halide is copper(I) iodide. Suitable bases for the reaction can include, but are not limited to, diisopropylamine, diethylamine, dipropylamine, triethylamine, isopropylethylamine, pyrrolidine, piperidine, or mixtures thereof. The preferred base is diisopropylamine. Suitable solvents for the reaction can include, but are not limited to, acetonitrile, ethyl acetate, isopropyl acetate, tetrahydrofuran, and mixtures thereof. The preferred solvent is acetonitrile. Typically, the amine of formula (VII) is reacted with the compound of formula (III-a) in an amount of from about 1:1 to about 1:3 molar equivalents, relative to the compound of formula (III-a). It is preferred that two molar equivalents of amine are reacted with one molar equivalent of a compound of formula (III-a). Under the preferred conditions, the reaction is carried out with copper (I) iodide in diisopropylamine in the presence of a PdCl₂(Ph₃P)₂ catalyst.

One with skill in the art may understand that compounds of formulae (III), (III-a), (IV), (V), (VI), and (VI-a ), wherein $R_A$ or $R_{A1}$ is bromo or chloro, can be treated with a boronic acid of the formula:

(HO)₂B—R₁                                          (VIII), wherein $R_1$ is 4-cyanophenyl, aryl, or heteroaryl, to provide a corresponding compound of each respective formula, wherein $R_A$ is 4-cyanophenyl, aryl, or heteroaryl. The phenyl portion of the 4-cyanophenyl, the aryl, and the heteroaryl can be substituted with 0, 1, 2, 3, or 4 substituents independently selected from alkoxy, alkoxyalkyl, alkyl, alkylthio, alkylthioalkyl, cyano, haloalkoxy, and haloalkyl, as previously described for compounds of formula (I) More particularly, the process is preferred for compounds wherein $R_1$ is 4-cyanophenyl.

Boronic acid esters of formula (VII-a) also can be substituted for boronic acids of formula (VIII)

(R_eO)(R_fO)B—R₁                                   (VIII-a).

The $R_e$ and $R_f$ in compounds of formula (VIII-a) are alkyl, or alternatively $R_e$ and $R_f$ taken together to form a ring, preferably a $C_1$–$C_6$ ring, wherein the ring can be substituted with 0, 1, 2, 3, or 4 alkyl or aryl groups and $R_1$ is as defined for compounds of formula (VIII). Examples of suitable compounds of formula (VIII-a) include, but are not limited to, (CH₃O)₂BPh, (4-cyanomethylphenyl)boronic acid, pinacol ester (CombiBlocks Inc., San Diego).

Boronic acids of formula (VIII) are commercially available or can be prepared by methods well known to those skilled in the art of synthetic organic chemistry. For example, Takagi et al. (Tetrahedron Letters, (2002) 43, 5649–5651) describe preparing heteroaryl pinacolborane esters of formula (VIII-a) using heteroaromatic compounds and reaction with bis(pinacolborane) in the presence of an iridium catalysis of IrCl[COD]2-(4,4'-di-t-butyl-2,2'-bipyridine) in octane. Other methods have been described wherein aryl halides and triflates and heteroaryl halides and triflates are reacted with alkyl lithiums or Grignard reagents, treated with trialkylborate esters, and then treated with acid to produce compounds of the formula (Vil) or (VIII-a). See, for example, B. T. O'Neill, et al. Organic Letters (2000), 2, 4201; M. D. Sindkhedkar, et al. Tetrahedron (2001), 57, 2991; W. C. Black, et al. Journal of Medicinal Chemistry (1999), 42, 1274; Letsinger; Dandegaonker; J. Amer. Chem. Soc. (1959), 81, 498, 501; Carroll, F. Ivy, et al. J. Med. Chem. (2001) 2229 –2237. Another well-known method is the Miyaura reaction described in: Ishiyama, Tatsuo; Ishida, Kousaku; Miyaura, Norio; Tetrahedron (2001) 9813 –9816, in which aryl and heteroaryl halides are reacted with bis (pinacolborane), KOAc, and Pd₂dba₃ and tris-cyclohexylphosphine or PdCl₂dppf (Ishiyama, et al. Tetrahedron (2001) 9813–9816). Examples of suitable boronic acids include, but are not limited to, 4-cyanophenylboronic acid, pyridine-3-boronic acid, pyrimidine-5-boronic acid pinacol ester, and the like. The preferred boronic acid is 4-cyanophenylboronic acid. The reaction provides the corresponding compound wherein the bromo substituent is replaced with a 4-cyanophenyl, aryl, or heteroaryl, as shown below:

Schemes 3–6

Scheme 3:

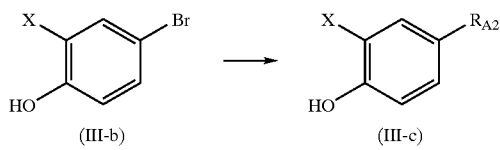

(III-b)                                             (III-c)

Scheme 4:

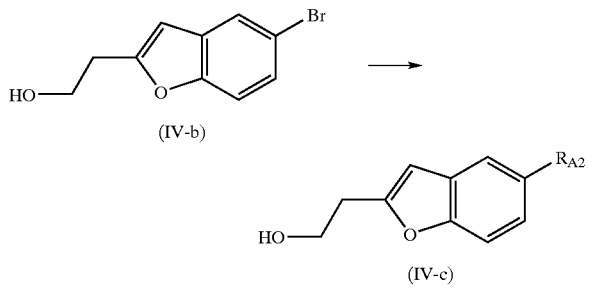

(IV-b)

(IV-c)

Scheme 5:

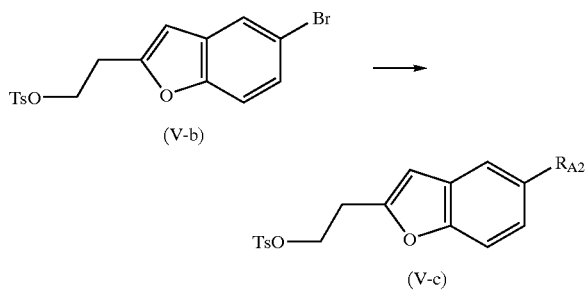

Scheme 6:

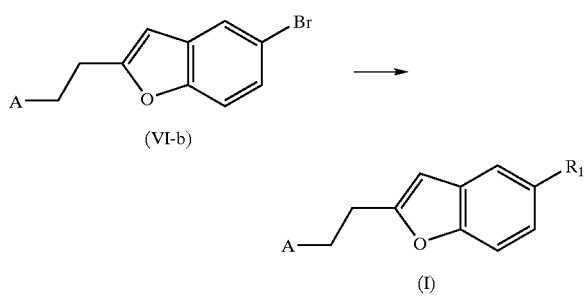

The group represented by $R_{A2}$ in compounds of formula (III-c), (IV-c), and (V-c) and $R_1$ in compounds of formula (I) in Schemes 3–6, represent a 4-cyanophenyl group, aryl, or a heteroaryl group. The process of the invention is particularly beneficial for compounds wherein $R_{A2}$ or $R_1$ is 4-cyanophenyl.

In addition, compounds of formula (VI)

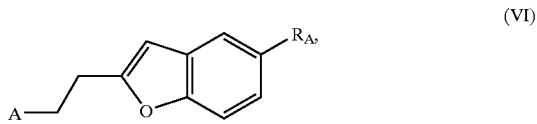

wherein $R_A$ is 4-cyanophenyl, aryl, or heteroaryl and A is as previously defined can be, but need not be, isolated and purified to provide compounds of formula (I). In one aspect, the compound of formula (VI) or (VI-a) can be isolated and purified, typically by chromatographic methods, using conventional methods in the art to provide a desired compound.

Examples of conventional methods for isolating and purifying compounds of formula (VI) or (VI-a) can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Alternatively, and more preferably, a compound of formula (VI) can be treated with an acid to form a desired salt. For example, a compound of formula (VI) or (VI-a) is reacted with an acid at above room temperature to provide the desired salt. Examples of acids suitable for the reaction include, but are not limited to, tartaric acid, lactic acid, succinic acid, as well as mandelic, atrolactic, methanesulfonic, hydrochloric, hydrobromic, phosphoric, sulfuric, citric, or hydroxybutyric acid, and the like. A preferred acid is tartaric acid and, more specifically, (L)-tartaric acid. Typically, the reaction is accomplished at above room temperature. Preferably, the reaction is carried out in a temperature of from about 50° C. to about 75° C. The preferred temperature for the reaction is about 60° C. After cooling, the desired salt can be isolated by filtration in pure form. The recrystallization procedure may be repeated to afford product of even higher purity.

The processes of the invention are particularly useful for preparing 4-(2-{2-[(2R)-2-methyl-1-pyrrolidinyl]ethyl}-1-benzofuran-5-yl)benzonitrile and salts thereof. A particular example of a process for preparing 4-(2-{2-[(2R)-2-methyl-1-pyrrolidinyl]ethyl}-1-benzofuran-5-yl)benzonitrile, and salts thereof, comprises the steps of:

(a) treating 4'-hydroxy-1,1'-biphenyl4-carbonitrile with N-iodosuccinimide and an acid, such as sulfuric acid, to provide 4'-hydroxy-3'-iodo-1,1'-biphenyl-4-carbonitrile;

(b) treating 4'-hydroxy-3'-iodo-1,1'-biphenyl-4-carbonitrile with 3-butyn-1-ol, a palladium source with a phosphine for the palladium and a metal halide in the presence of a base, for example using palladium(ll) acetate, triphenylphosphine, copper(I) iodide in the presence of diisopropylamine, in isopropyl acetate to provide 4-[2-(2-hydroxyethyl)-1-benzofuran-5-yl] benzonitrile;

(c) reacting 4-[2-(2-hydroxyethyl)-1-benzofuran-5-yl] benzonitrile with para-toluenesulfonyl chloride and N,N-dimethylaminopyridine, in the presence of a base, such as triethylamine, to provide 2-[5-(4-cyanophenyl)-1-benzofuran-2-yl]ethyl 4-methylbenzenesulfonate; and (d) treating 2-[5-(4-cyanophenyl)-1-benzofuran-2-yl] ethyl 4-methylbenzenesulfonate with (2R)-2-methylpyrrolidine, preferably in the presence of potassium carbonate and in an acetonitrile solvent, to provide 4-(2-{2-[(2R)-2-methyl-1-pyrrolidinyl]ethyl}-1-benzofuran-5-yl)benzonitrile.

Yet another aspect of the invention relates to preparing a compound of formula (III), which provides useful intermediates in the preparation of amine-substituted benzofuran derivatives described herein. Such process comprises the step of reacting a phenol of formula (II) with a suitable halogenating reagent, as shown in Scheme 7, below.

Scheme 7

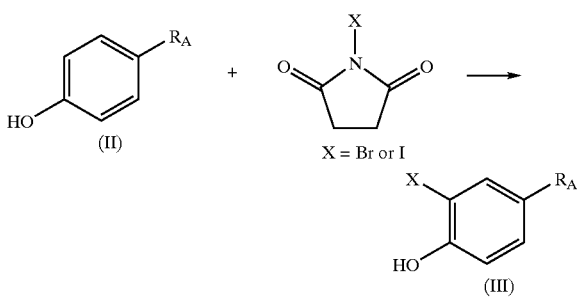

X = Br or I

As shown in Scheme 7, compounds of formula (II) wherein $R_A$ is selected from the group consisting of bromo, chloro, 4-cyanophenyl, aryl, and heteroaryl, as previously described with compounds of formula (II) can be reacted with a halogenating reagent selected from N-bromosuccinimide and N-iodosuccinimide. The reagents and conditions are as described for preparing compounds of formula (III) according to Scheme 1. The compound of formula (III) suitably can be used to prepare compounds of formula (I), for example by processes described herein.

Yet another aspect of the invention relates to compounds of formula (V), wherein $R_B$ is toluenesulfonate, particularly wherein $R_A$ is 4-cyanophenyl, and compounds of formulae (I), (III), (VI), and (VI-a) prepared by the processes described above.

Still yet another aspect of the invention relates to a compound of the formula (IX),

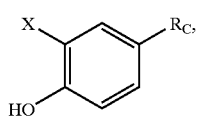

(IX)

wherein X is bromo or iodo and $R_c$ is 4-cyanophenyl, wherein the phenyl portion of 4-cyanophenyl is substituted with 0, 1, 2, 3, or 4 substituents selected from the group consisting of alkoxy, alkoxyalkyl, alkyl, alkylthio, alkylthioalkyl, cyano, haloalkoxy, halogen, and haloalkyl. Preferably, $R_c$ is 4-cyanophenyl without additional substituents on the phenyl moiety. The compound can be used as an intermediate or starting material for preparing compounds of formula (I), which also is contemplated as an aspect of the invention.

The processes of the invention, and intermediates and products prepared by the processes, can be better understood in connection with the following examples, which are merely intended to illustrate the invention and should not be construed to limit the invention in any way.

REFERENCE EXAMPLE

Preparation of (2R)-2-methylpyrrolidine and (2S)-2-methylpyrrolidine (2R)-2-Methylpyrrolidine tartrate was prepared by the resolution of racemic (+/−) 2-methylpyrrolidine with L-tartaric acid (which is also called (2R,3R)-(+)-tartaric acid, Chemical Abstracts number 87-69-4, available from Aldrich Chemical Co., Milwaukee, Wis.) using enantioselective recrystallization procedures as described by William Gaffield, et al. in Tetrahedron, 37:1861–1869 (1981), or in Karrer and Ehrhardt in Helv.Chim.Acta, 34: 2202, 2208 (1951). (2R)-2-methylpyrrolidine hydrobromide also is a suitable source of (2R)-2-methylpyrrolidine, and was prepared from L-prolinol (which also called (S)-(+)-pyrrolidinemethanol, Chemical Abstracts number 23356-96-9, Aldrich Chemical Co., Milwaukee, Wis.) using the procedure described by Nijhuis, Walter H.N., et al., J.Org.Chem., 54(1): 209–216, 214 (1989). Other procedures describing the synthesis of R-2-methylpyrrolidine and salts thereof can be found in Andres, Jose M., et al. Eur.J.Org.Chem., 9:1719–1726 (2000); and Elworthy, Todd R.; Meyers, A. I., Tetrahedron, 50(20): 6089–6096 (1994).

(2S)-2-Methylpyrrolidine can be substituted for (2R)-2-methylpyrrolidine in the experimental procedures provided herein. The (2S)-2-methylpyrrolidine can be prepared by procedures described in Kim, Mahn-Joo, et al., Bioorg.Med. Chem.Lett. 6(1):71–76 (1996).

EXAMPLES

Example 1

4-(2-{2-[(2R)-2-methyl-1-pyrrolidinyl]ethyl}-1-benzofuran-5-yl)benzonitrile (L) Tartrate Example 1A 3'-lodo-4'-hydroxy-1,1'-biphenyl4-carbonitrile 4'-Hydroxy-1,1'-biphenyl-4-carbonitrile (2.15 kg, 10.90 mol), purchased from Takeda Chemical Industries, Tokyo, Japan, and N-iodosuccinimide (2.4 kg, 97% pure, 10.36 mmol) were combined in acetic acid (17.2 L) at room temperature under nitrogen. The suspension was treated with sulfuric acid (290 mL) slowly maintaining the temperature below 27° C. The reaction was stirred at room temperature and the reaction progress was monitored by HPLC. The reaction mixture was treated with distilled water (35 L) while maintaining the temperature below 30° C. After stirring at room temperature for 1 hour, the solid was filtered and the filter cake was washed with distilled water (32 L) to afford a solid. The solid was dried under reduced pressure at 60° C. for 48 hours to provide the title compound. MS (ESI-) (M-H)⁻ 320; ¹H-NMR (DMSO-d₆) δ 10.75 (1H, s), 8.05 (1H, d, J=2.3 Hz), 7.83 (2H, m), 7.80 (2H, m), 7.62 (1H, dd, J=6.1, 8.5 Hz), 7.00 (1H, d, J=8.5 Hz); ¹³C-NMR (DMSO-d₆) δ 156.84, 142.55, 136.63, 132.27, 130.52, 127.91, 126.36, 118.54, 114.96, 108.89, 85.32.

Example 1B

4-[2-(2-hydroxyethyl)-1-benzofuran-5-yl] benzonitrile

The product from Example 1A (3.1 kg, 9.68 mol) in isopropyl acetate (49.2 kg) was purged with N₂ for about 10 minutes and then cooled to about 15° C. The mixture was treated with palladium(ll) acetate (22 g, 0.10 mol), triphenylphosphine, (51 g, 0.19 mol), copper(I) iodide (38 g, 0.19 mol), and 3-butyn-1-ol (0.91 kg, 12.59 moles) while continuing to purge with N₂. The mixture was then treated with diisopropylamine (1.97 kg, 19.37 mol), by addition over about 30 minutes. After 2 hours, the suspension was heated to about 40° C. After about 8 hours, the reaction mixture was cooled to room temperature and filtered through a pad of Celite®. The pad was washed with isopropyl acetate (12 kg) and the filtrate was washed with 5% NaHCO₃ solution and then washed with water. The organic layer was then distilled to dryness. The residue (2.03 kg, 80% assayed yield) was carried onto the tosylation step. A small sample was purified by silica gel chromatography. ¹H NMR (CDCl₃ at 400 MHz) δ1.81 (t, 1 H), 3.07 (t, 2H), 4.01 (q, 2H), 6.56 (s, 1H) 7.41–7.50 (m, 2H), 7.67 (m, 5H); ¹³C NMR (CDCl₃ at 100 MHz) δ 32.3, 60.6, 103.6, 110.1, 111.2, 118.8, 119.0, 122.8, 127.6, 129.3, 132.2, 133.8, 145.8, 154.6, 157.0 with 2 peaks overlapping.

Example 1C

2-[5-(4-cyanophenyl)-1-benzofuran-2-yl]ethyl 4-methylbenzenesulfonate

The product from Example 1B (2.03 kg, 7.71 mol) in acetonitrile (31.8 kg) was treated in succession with triethylamine (1.86 kg, 18.34 mol), 4-(dimethylamino)pyridine (0.10 kg, 0.87 mol), and p-toluenesulfonyl chloride (3.50 kg, 17.99 mol). After stirring at room temperature for about 5 hours, the reaction mixture was distilled to a minimum volume and treated with isopropyl alcohol (24.1 kg). The suspension was heated at about 30° C. for 1 hour, then cooled to about 5° C., filtered, and the filter cake was washed with isopropyl alcohol (5.20 kg). The solid was dried at 50° C. to provide 2.59 kg (80% yield) of the title compound. MS-DCI (M+NH$_4$)$^+$ m/z at 435; $^1$H NMR (CDCl$_3$ at 400 MHz) δ 2.38 (s, 3H), 3.15 (t, 2H), 4.38 (t, 2H), 6.50 (s, 1H) 7.18–7.24 (m, 2H), 7.37–7.46 (m, 2H), 7.67–7.74 (m, 7H); $^{13}$C NMR (CDCl$_3$ at 100 MHz) δ 21.9, 28.9, 67.2, 104.4, 110.3, 111.2, 118.7, 119.2, 123.0, 127.5, 127.6, 129.0, 129.4, 132.2, 132.4, 133.9, 144.4, 145.7, 154.1, 154.5.

Example 1D 4-(2-{2-[(2R)-2-methyl-1-pyrrolidinyl]ethyl}-1-benzofuran-5-yl)benzonitrile Potassium carbonate powder (2.28 kg, 16.5 mol, 325 mesh) and milled (2R)-2-methylpyrrolidine tartrate (1.78 kg, 7.48 mol) were combined in acetonitrile (37.4 kg) and heated at 55° C. with agitation for 36 hours. The mixture was chilled to about 25° C., and the product from Example 1C (2.07 kg, 4.98 mol) was added to the mixture in portions. The reaction mixture was heated at 65° C. with -agitation for about 48 hours. The mixture was cooled to about 25° C., filtered, and the filtrate was concentrated to a volume of about 10 L. The mixture was partitioned between toluene (32.3 kg) and 5% NaHCO$_3$ solution (23.7 kg). The organic phase was separated and washed with 5% NaHCO$_3$ solution (23.7 kg). The organic phase was then extracted with a mixture of CH$_3$SO$_3$H:N-methylpyrrolidinone:H$_2$O (10:20:70 v/v/v) (32 kg, 8.0 kg respectively). The extract was treated with isopropyl acetate (32.5 kg) and the pH adjusted to about 12 with 50% NaOH solution (about. 4.9 kg) at about 30° C. After stirring, the organic phase was separated and the aqueous phase was extracted with isopropyl acetate (IPAC) (6.0 kg). The organic phases were combined, washed with 5% NaHCO$_3$ (33 kg×3), distilled water (33 kg×2), distilled to a volume of about 10 L, and chased with IPAC (15.6 kg) to about 10 L. The mixture was diluted with isopropyl alcohol (14.5 kg) and concentrated to 10 L. Additional 14.5 kg of isopropyl alcohol was added and the solution concentrated to a volume of 10 L. The solution was treated with active carbon (Darco KB-B, 0.125 kg) and heated at 30° C. with stirring for 1 hour. The mixture was filtered through a pad of Celite® and the Celite® washed with isopropyl alcohol (6.3 kg). The filtrate (about 13 kg) was used directly in the next step (1.17 kg).

Example 1E 4-(2-{2-[(2R)-2-methyl-1-pyrrolidinyl]ethyl}-1-benzofuran-5-yl)benzonitrile (L)-tartrate The solution from Example 1D was diluted with absolute ethanol (5.0 kg), heated at 65° C., and treated with a solution of (L)-tartaric acid (0.56 kg, 3.73 mol) in absolute ethanol (8.0 kg) slowly. The mixture was cooled to about 25° C., agitated for about 16 hours, cooled to 0° C. for 2 hours, and filtered. The filter cake was washed with isopropyl alcohol (5.0 kg), dried at 60° C. for about 24 hours to provide 1.46 kg of the title compound as a solid (61% isolated yield from the tosylate). Mp 152–154 ° C.; $^1$H-NMR (DMSO-d$_6$) δ 7.8–8.0 (5H, m), 7.62 (2H, m), 6.80 (1H, s), 4.10 (2H, s), 3.40 (2H, m), 3.25 (2H, m), 2.95 (2H, m), 2.70 (1H, q), 2.02 (1H, m), 1.80 (2H, m), 1.48 (2H, m), 1.22 (3H, d, J=6.6 Hz); $^{13}$C-NMR (DMSO-d$_6$) δ 174.3, 157.6, 154.6, 145.4, 133.6, 133.0, 129.5, 127.9, 123.2, 119.5, 119.1, 111.5, 109.7, 103.7, 72.3, 61.3, 52.5, 50.1, 31.5, 25.7, 21.1, 16.8; Anal: C$_{26}$H$_{28}$N$_2$O$_7$. ½ H$_2$O; Calc'd C%=63.80, H%=5.93, N%=5.72, O%=24.53; Found. 63.55, 5.60, 5.64, 25.18.

Example 2

4-(2-{2-[(2R)-2-methyl-1-pyrrolidinyl]ethyl}-1-benzofuran-5-yl)benzonitrile (L)-tartrate

Example 2A (2R)-1-(3-butynyl)-2-methylpyrrolidine

A sealed pressure tube was charged potassium carbonate powder (18.4 g, 133.2 mmol, 325 mesh), milled (2R)-2-methylpyrrolidine tartrate (20.9 g, 88.8 mmol), 3-butynyl 4-methylbenzenesulfonate (15.7 mL, 88.8 mmol), and acetonitrile (105 mL). The mixture was heated at 85° C. and stirred for 16 hours. The completion of the reaction was monitored by gas chromatography until all the tosylate was consumed. The reaction mixture was cooled to room temperature, diluted with CH$_3$CN (50 mL), and filtered. The filtrate was used in the next step without further purification. GC-MS m/z 138 (M+H)$^+$.

Example 2B 4-(2-{2-[(2R)-2-methyl-1-pyrrolidinyl]ethyl}-1-benzofuran-5-yl)benzonitrile The solution from Example 2A (3.02 g, 22.0 mmol) in CH$_3$CN (49.5 mL) was purged with nitrogen and treated with the product from Example 1A (3.21 g, 10.0 mmol), CuI (38 mg, 0.2 mmol), PdCl$_2$(Ph$_3$P)$_2$(70 mg, 0.2 mmol), and diisopropylamine (8.4 ml, 60 mmol). The mixture was stirred at room temperature under nitrogen until reaction was near complete by HPLC. The reaction mixture was concentrated to about 30 mL, treated with toluene (100 mL), washed with 5% NaHCO$_3$ (2×100 mL), and 10% NH$_4$Cl (2×100 mL). The organic layer was separated, filtered through a pad of Celite®, and extracted with (CH$_3$SO$_3$H:N-methylpyrrolidinone:H$_2$O, 10:20:70) (2×100 mL). The aqueous layer was extracted with IPAC (2×100 mL), basified with 50% NaOH, and extracted with IPAC (2×100). The organic layer was washed with 5% NaHCO$_3$ (2×100 mL), 25% brine (100 mL), and treated with active carbon, silica gel (6.0 g), and Na$_2$SO$_3$ (1.0 g). The mixture was stirred at room temperature for 1 hour and filtered. The filtrate was concentrated to dryness to provide the title compound.

Example 2C 4-(2-{2-R[(2R)-2-methyl-1-pyrrolidinyl]ethyl}-1-benzofuran-5-yl)benzonitrile (L)-tartrate The product from Example 2B in isopropyl alcohol (IPA) (32 mL) and ethanol (12 mL) was treated with a solution of (L)-tartaric acid (1.0 g in 20 mL of EtOH) and heated at 60° C. The mixture was allowed to cool to room temperature and stirred overnight. The mixture was cooled at 0° C. for 2 hours, filtered, and the filter cake dried at 65° C. under reduced pressure overnight to provide the title compound as a solid. Mp 152–154° C.; 99% pure by HPLC; $^1$H-NMR (DMSO-d$_6$) δ 7.8–8.0 (5H, m), 7.62 (2H, m), 6.80 (1H, s), 4.10 (2H, s), 3.40 (2H, m), 3.25 (2H, m), 2.95 (2H, m), 2.70 (1H, q), 2.02 (1H, m), 1.80 (2H, m), 1.48 (2H, m), 1.22 (3H, d, J=6.6 Hz); $^{13}$C-NMR (DMSO-d$_6$) δ 174.3, 157.6, 154.6, 145.4, 133.6, 133.0, 129.5, 127.9, 123.2, 119.5, 119.1, 111.5, 109.7, 103.7, 72.3, 61.3, 52.5, 50.1, 31.5, 25.7, 21.1, 16.8.

Example 3

4-(2-{2-[(2R)-2-methyl-1-pyrrolidinyl]ethyl}-1-benzofuran-5-yl)benzonitrile (L)-tartrate

Example 3A

4-bromo-2-iodophenol

4-Bromophenol (51.9 g, 0.30 mol) and N-iodosuccinimide (67.5 g, 0.30 mol) were combined in acetic acid (360 mL). The mixture was stirred briefly, treated with concentrated sulfuric acid (5 mL, 0.09 mol) and stirred at about 22° C. overnight. The mixture was poured into water (about 800 mL) with stirring to precipitate the product. The suspension was stirred for about 1 hour and filtered. The wet cake was washed with water (50 mL, 2×) and dried under reduced pressure at about 50° C. (80.9 g, 90%). MS-DEI (M+H)$^+$ m/z at 298; $^1$H NMR (CDCl$_3$ at 400 MHz) δ 5.28 (s,1H), 6.86 (d, 1H), 7.33 (dd, 1H), 7.75 (d, 1H); $^{13}$C NMR (CDCl$_3$ at 100 MHz) δ 86.0, 112.8, 116.0, 132.7, 139.4, 153.7.

Example 3B

(2R)-1-[2-(5-bromo-1-benzofuran-2-yl)ethyl]-2-methylpyrrolidine (2R)-2-Methylpyrrolidine tartrate (1.17 g, 5.0 mmol), and potassium carbonate (1.38 g, 10.0 mmol) were combined in acetonitrile (20 mL) and heated at 60° C. for 1 hour. The mixture was treated with 3-butynyl 4-methylbenzenesulfonate (673 mg, 3.0 mmol) and heated at about 60° C. overnight. The mixture was cooled to about 5° C. and filtered. The mixture was treated with the product from Example 3A (300 mg, 1.0 mmol), diisopropylamine (1.20 g, 11.8 mmol), dichlorobis(triphenylphosphine)palladium (II) (35.1 mg, 0.05 mmol), and copper iodide (38.0 mg, 0.20 mmol). After stirring overnight at about 30° C., the mixture was concentrated to dryness. The residue in ethyl acetate (20 mL) was washed with 5% NaHCO$_3$ (20 mL×2) and 25% brine (25 mL). The organic phase was separated, dried over anhydrous Na$_2$SO$_4$, filtered, and the filtrate concentrated to dryness to provide the title compound. MS (esi): 308, 310 (M+H)$^+$; $^1$H-NMR (CDCl$_3$) δ 7.58 (1H, d, J=1.7 Hz), 7.27 (2H, m), 6.38 (1H, s), 3.20 (2H, m), 2.95 (2H, m), 2.43 (1H, m), 2.28 (1H, m), 2.19 (1H, q, J=8.8 Hz), 1.95 (1H, m), 1.75 (2H, m), 1.42 (1H, m), 1.13 (3H, d, J=6.2 Hz); $^{13}$C-NMR (CDCl$_3$) δ 158.8, 152.9,130.6, 125.7, 122.6, 115.2,111.9, 101.8, 60.0, 53.9, 51.9, 32.9, 28.4, 22.0, 19.3.

Example 3C

4-(2-{2-[(2R)-2-methyl-1-pyrrolidinyl]ethyl}-1-benzofu ran-5-yl)benzonitrile (L)-tartrate The product from Example 3B (116 mg, 0.375 mmol), 4-cyanophenylboronic acid (83 mg, 0.56 mmol), tetrakis(triphenylphosphine)palladium (0) (43.3 mg, 0.0375 mmol), 2-(dicyclohexylphosphino)biphenyl (26.2 mg, 0.075 mmol), and sodium carbonate (60 mg, 0.57 mmol) were combined in 1,2-dimethoxyethane (6 mL) and water (2 mL). The reaction mixture was heated at 80° C. for 5 hours, allowed to cool to room temperature, and diluted with ethyl acetate (15 mL). The mixture was washed with 5% NaHCO$_3$, 25% brine, dried over anhydrous Na$_2$SO$_4$, filtered, and the filtrate was concentrated to dryness. The residue was purified by silica gel column chromatography to provide the free base (92 mg), which was converted to the corresponding (L)-tartrate (58 mg, 32% yield); mp: 156–157° C. (uncorrected); MS (esi): 331 (M+1); $^1$H-NMR (DMSO-d$_6$) δ 7.90 (5H, m), 7.62 (2H, m), 6.79 (1H, s), 4.10 (2H, s), 3.40 (2H, m) 3.08 (2H, m), 2.90 (2H, m), 2.63 (1H, q, J=8.8 Hz), 2.02 (1H, m), 1.80 (2H, m), 1.43 (1H, m), 1.20 (3H, d, J=6.3 Hz); $^{13}$C-NMR (DMSO-d$_6$) δ 173.1,156.7,153.7, 144.6, 132.8, 132.2, 128.8, 127.2, 122.5, 118.9, 118.5, 110.9, 109.1,103.2, 71.7, 61.0, 52.5, 50.1, 31.6, 26.0, 21.2, 17.1.

Example 4

4-(2-{2-[(2R)-2-methyl-1-pyrrolidinyl]ethyl}-1-benzofuran-5-yl)benzonitrile

Example 4A

2-(5-bromo-1-benzofuran-2-yl)ethanol

The product from Example 3A (14.95 g, 50 mmol), palladium(ll) acetate (0.11 g, 0.5 mmol), triphenylphosphine (0.26 g, 1.0 mmol), and copper(I) iodide (0.19 g, 1.0 mmol) were combined in isopropyl acetate (100 mL). Nitrogen gas was bubbled through the reaction mixture for about 15 minutes. The mixture was treated with 3-butyn-1-ol (5.6 mL, 75.0 mmol) stirred briefly and then treated with diisopropylamine (42 mL, 300 mmol) slowly over about 10 minutes. After stirring for 2 hours at about 22° C., the mixture was heated at about 60° C. for about 6 hours and then cooled to about 22° C. The reaction mixture was filtered through a pad of Celite® (~5 g) and the Celite® was washed with isopropyl acetate (~30 mL). The filtrate was washed with saturated NaHCO$_3$ solution (100 mL, 2×), 10% Na$_2$S$_2$O$_3$ solution (100 mL, 2×), brine (50 mL), dried over Na$_2$SO$_4$, and distilled to dryness. The residue was purified by silica gel column chromatography to provide the title compound (8.7 g, 72% yield). MS DCl (M+NH$_4$)$^+$ m/z at 258,260; $^1$H NMR(CDCl$_3$ at 400 MHz) δ 3.03 (m, 2H), 3.98 (m, 2H), 6.45 (m, 1H), 7.25–7.32 (m, 2H), 7.60 (d, 1H); $^{13}$C NMR (CDCl$_3$ at 100 MHz) δ 32.2, 60.6, 103.0, 112.1, 115.4, 122.8, 126.1, 130.4, 153.1, 157.0.

Example 4B

2-(5-bromo-1-benzofuran-2-yl)ethyl 4-methylbenzenesulfonate

The product from Example 4A (1.21 g, 5.0 mmol), 4-dimethylaminopyridine (0.06 g, 0.5 mmol), and triethylamine (1.5 mL, 10.5 mmol) were combined in dichloromethane (20 mL) stirred briefly and treated with para-toluenesulfonyl chloride (1.91 g, 10.0 mmol) in dichloromethane (2 mL) over about 5 minutes. After stirring at about 22° C. for 3 hours, the mixture was then washed with saturated NaHCO$_3$ solution (20 mL, 2×), brine (20 mL), dried over Na$_2$SO$_4$, and distilled to dryness. The residue in acetonitrile (~5 mL) was heated at 50° C. to effect dissolution, allowed to cool to room temperature slowly, and then cooled to about 0° C. The slurry was filtered and the obtained solid dried under reduced pressure at 40° C. to provide the title compound (0.95 g, 48% yield). MS-DCI (M+NH$_4$)$^+$ observed m/z at 412, 414; $^1$H NMR (CDCl$_3$ at 400 MHz) δ 2.38 (s, 3H), 3.11 (m, 2H), 4.35 (m, 2H), 6.35 (m, 1H), 7.1–7.18 (m, 3H), 7.27 (dd, 1H), 7.56 (d, 1H), 7.64–7.67 (m, 2H); $^{13}$C NMR (CDCl$_3$ at 100 MHz) δ 21.9, 28.8, 67.1, 103.7, 112.0, 115.5, 122.9, 126.3, 127.4, 129.4, 130.1, 132.3, 144.4, 153.0, 154.2 with 2 peaks overlapping.

Example 4C

(2R)-1-[2-(5-bromo-1-benzofuran-2-yl)ethyl]-2-methylpyrrolidine (2R)-2-Methylpyrrolidine tartrate (0.70 g, 3.0 mmol) and potassium carbonate (0.82 g, 6.0 mmol) were combined in acetonitrile (12 mL). The slurry was heated at 60° C. for 1 hour, treated with the product from Example 4B (790 mg, 2.0 mmol). The mixture was heated at about 60° C. for 6 hours, cooled to 25° C., and diluted with toluene (30 mL). The mixture was washed with 5% NaHCO$_3$ (40 mL×2) and extracted with H$_2$O: N-methylpyrrolidinone: MSA (methanesulfonic acid)=70:20:10 (30 mL). The aqueous solution was adjusted to pH about 12 with 50% NaOH and extracted with IPAC (45 mL). The organic phase was washed with 5% NaHCO$_3$ (50 mL×3), water (50 mL, 2×), dried over MgSO$_4$, filtered, and the filtrate was concentrated to dryness to provide 375 mg (60%) of the title compound. MS (esi): 308, 310 (M+H)$^+$; $^1$H-NMR (CDCl$_3$) δ 7.58 (1H, d, J=1.7 Hz), 7.27 (2H, m), 6.38 (1H, s), 3.20 (2 H, m), 2.95 (2H, m), 2.43 (1H, m), 2.28 (1H, m), 2.19 (1H, q, J=8.8 Hz), 1.95 (1 H, m), 1.75 (2H, m), 1.42 (1H, m), 1.13 (3H, d, J=6.2 Hz); $^{13}$C-NMR (CDCl$_3$) δ 158.8, 152.9, 130.6, 125.7, 122.6, 115.2, 111.9, 101.8, 60.0, 53.9, 51.9, 32.9, 28.4, 22.0, 19.3.

Example 4D 4-(2-{2-[(2R)-2-methyl-1-pyrrolidinyl]ethyl}-1-benzofuran-5-yl)benzonitrile The title compound can be prepared using the procedure described in Example 3C.

Example 5

4-[2-(2-hydroxyethyl)-1-benzofuran-5-yl]benzonitrile

The product from Example 4A (241 mg, 1.0 mmol), 4-cyanophenylboronic acid (221 mg, 1.5 mmol), tetrakis (triphenylphosphine) palladium (0) (57.5 mg, 0.05 mmol), 2-(dicyclohexyl phosphino)biphenyl (35.0 mg, 0.10 mmol), and sodium carbonate (160 mg, 1.5 mmol) were combined in 1,2-dimethoxyethane (16 mL) and water (6 mL) and heated at 80° C. overnight. The mixture was allowed to cool to room temperature and diluted with ethyl acetate (30 mL). The mixture was washed with 5% NaHCO$_3$, 25% brine, dried over anhydrous Na$_2$SO$_4$, filtered, and the filtrate was concentrated to dryness. The residue was purified by silica gel column chromatography to provide 197 mg (75%) of the title compound. An analytical sample was crystallized from diethyl ether; mp; MS-DCl-NH$_3$: 281 (M+NH$_4$)$^+$; $^1$H-NMR (CDCl$_3$) δ 7.68 (5H, m), 7.51 (1H, d, J=8.5Hz), 7.44 (1H, dd, J=8.5, 1.9 Hz), 6.57 (1H, s), 4.02 (2H, q, J=5.8 Hz), 3.07 (2H, t, J=5.8Hz) 1.70 (1H, t, J=5.8Hz), $^{13}$C-NMR (CDCl$_3$) δ 156.9, 154.6, 145.8, 133.9, 132.2, 129.3, 127.6, 122.8, 119.0, 118.8, 111.2, 110.2, 103.7, 60.7, 32.3.

Example 6

4-(2-{2-[(2S)-2-methyl-1-pyrrolidinyl]ethyl}-1-benzofu ran-5-yl)benzonitrile

4-{2-[2-(2(S)-Methyl-pyrrolidin-1-yl)-ethyl]-benzofuran-5-yl}-benzonitrile can be prepared by the method described in Examples 2A and 2B, except that (S)-2-methylpyrrolidine tartrate is used in the place of (2R)-2-methylpyrrolidine tartrate in step 2A.

Examples 7–15

The following compounds can be prepared by using the methods described in Example 3c, but substituting the corresponding boronic acid and boronic acid ester compounds in place of 4-cyanophenylboronic acid as shown below in Table 1.

TABLE 1

| Example | Compound | Reagent | Commercial Source, Chemical Abstracts Number or Literature Reference |
|---|---|---|---|
| 7 | 5-{2-[2-(2(R)-methyl-pyrrolidin-1-yl)-ethyl]-benzofuran-5-yl}-1H-pyrimidin-2-one | 2-pyrimidinone-5-boronic acid | Matrix Scientific, Columbia, SC, USA |
| 8 | 5-{2-[2-(2(R)-methyl-pyrrolidin-1-yl)-ethyl]-benzofuran-5-yl}-1H-pyrimidine-2,4-dione | 1H-pyrimidine-2,4-dione-5-boranic acid | Specs, Fleminglaan, the Netherlands |
| 9 | 3-{2-[2-(2(R)-methyl-pyrrolidin-1-yl)-ethyl]-benzofuran-5-yl}-pyridine | pyridine-3-boronic acid | CAS #1692-25-7, Frontier Scientific, Inc., Logan, UT, USA |
| 10 | 8-{2-[2-(2(R)-methyl-pyrrolidin-1-yl)-ethyl]-benzofuran-5-yl}-quinoline | 8-quinoline boronic acid | CAS #86-58-8, Matrix Scientific, Columbia, SC, USA |
| 11 | 2,4-dimethoxy-5-{2-[2-(2(R)-methyl-pyrrolidin-1-yl)-ethyl]-benzofuran-5-yl}-pyrimidine | 2,4-dimethoxypyrimidine-5-boronic acid | CAS #89641-18-9, Frontier Scientific, Inc., Logan, UT, USA |
| 12 | 2-methoxy-5-{2-[2-(2(R)-methyl-pyrrolidin-1-yl)-ethyl]-benzofuran-5-yl}-pyridine | 2-methoxy-5-pyridine boronic acid | Digital Specialty Chemicals, Dublin, NH, USA |
| 13 | 3-{2-[2-(2(R)-methyl-pyrrolidin-1-yl)-ethyl]-benzofuran-5-yl}-quinoline | 3-quinoline boronic acid | Digital Specialty Chemicals, Dublin, NH, USA |

TABLE 1-continued

| Example | Compound | Reagent | Commercial Source, Chemical Abstracts Number or Literature Reference |
|---|---|---|---|
| 14 | 5-{2-[2-(2(R)-methyl-pyrrolidin-1-yl)-ethyl]-benzofuran-5-yl}-pyrimidine | pyrimidine-5-boronic acid | Gronowitz, S.; Hoernfeldt, A. B.; Kristjansson, V.; Musil, T. On the synthesis of various thienyl- and selenienylpyrimidines. Chem. Scr. (1986), 26(2), 305–9. |
| 15 | 5-{2-[2-(2(R)-methyl-pyrrolidin-1-yl)-ethyl]-benzofuran-5-yl}-pyrimidine | pyrimidine-5-boronic acid, pinacol ester | Umemoto, Kazuhiko; Tsukui, Hitoshi; Kusukawa, Takahiro; Biradha, Kumar; Fujita, Makoto; Angew.Chem.Int.Ed.; 40; 14; 2001; 2620–2622. |

Various changes and modifications to the disclosed embodiments will be apparent to those skilled in the art. Such changes and modifications are within the purview of the invention and can be made without departing from the spirit and scope thereof. The foregoing detailed descriptions are merely illustrative of the invention and are not intended to limit the scope of the invention, which is defined solely by the scope of the appended claims.

What is claimed is:

1. A process for preparing a compound of formula (I):

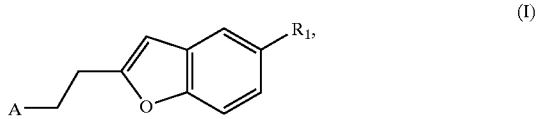

(I)

or a salt thereof, wherein

A is heterocyclic group selected from pyrrolidinyl or piperidinyl, wherein the heterocycle is substituted with 0, 1, 2, 3, or 4 substituents selected from the group consisting of alkyl and fluoroalkyl; and $R_1$ is 4-cyanophenyl, the process comprising the steps of:

(6a) treating a compound of formula (III-a),

(III-a)

wherein $R_{A1}$ is selected the group consisting of bromo chloro, 4-cyanophenyl; with a compound of formula (VII),

(VII)

wherein A is a heterocylic group selected from the group consisting of pyrrolidinyl and piperidinyl, said heterocyclic group substituted with 0, 1, 2, 3, or 4 substituents selected from the group consisting of alkyl and fluoroalkyl, to provide a compound of formula (VI-a),

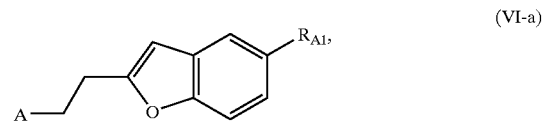

(VI-a)

wherein $R_{A1}$ and A are as defined above; and (6b) further treating the compound of formula (VI-a), wherein $R_{A1}$ is bromo or chloro, with a compound of formula (VIII),

(VIII), or a compound of formula (VIII-a),

(VIII-a), wherein $R_1$ is 4-cyanophenyl; and $R_e$ and $R_f$ are each independently alkyl or $R_e$ and $R_f$ are taken together to form a ring, wherein the ring is substituted with 0, 1, 2, 3, or 4 substituents selected from the group consisting of alkyl or aryl.

2. The process according to claim 1 wherein the compound of formula (III-a) in step 6a is reacted with the compound of formula (VII) and a palladium catalyst, metal halide, and base, wherein the palladium catalyst is selected from the group consisting of tetrakis(triphenylphosphine) palladium, (dibenzylideneacetate)palladium, (tris (dibenzylideneacetate)dipalladium, bis (tricyclohexylphosphine)palladium, (2-(diphenylphosphino) ethyl)palladium, (1,1 '-bis(diphenylphosphino)ferrocene) palladium, bis(triphenylphosphine)dichloropalladium, bis (1,1'-bis(diphenylphosphino)ferrocene)palladium, bis(2-(diphenylphosphino)ethyl)dichloropalladium, and $PdCl_2$ $(CH_3CN)_2$.

3. The process according to claim 2 wherein the palladium catalyst is bis(triphenylphosphine)dichloropalladium ($PdCl_2$ $(Ph_3P)_2$).

4. The process according to claim 2 wherein the metal halide is copper(I) iodide and the base is diisopropylamine.

5. The process according to claim 1 wherein A is (2R)-2-methylpyrrolidinyl.

* * * * *